(12) United States Patent
Barkenbus et al.

(10) Patent No.: US 10,603,043 B2
(45) Date of Patent: Mar. 31, 2020

(54) OCCLUSION DEVICE FOR A VASCULAR OR BIOLOGICAL LUMEN

(71) Applicant: ENDOSHAPE, INC., Boulder, CO (US)

(72) Inventors: Charles Barkenbus, Longmont, CO (US); Jeffrey Castleberry, Longmont, CO (US); Julie Trommeter, Denver, CO (US); William Aldrich, Napa, CA (US)

(73) Assignee: Endoshape, Inc., Boulder, CO (US)

( * ) Notice: Subject to any disclaimer, the term of this patent is extended or adjusted under 35 U.S.C. 154(b) by 1069 days.

(21) Appl. No.: 14/372,668

(22) PCT Filed: Jan. 17, 2013

(86) PCT No.: PCT/US2013/021987
§ 371 (c)(1),
(2) Date: Jul. 16, 2014

(87) PCT Pub. No.: WO2013/109784
PCT Pub. Date: Jul. 25, 2013

(65) Prior Publication Data
US 2015/0257765 A1    Sep. 17, 2015

Related U.S. Application Data

(60) Provisional application No. 61/587,518, filed on Jan. 17, 2012, provisional application No. 61/641,145, filed on May 1, 2012.

(51) Int. Cl.
*A61B 17/12* (2006.01)
*A61M 5/00* (2006.01)
(Continued)

(52) U.S. Cl.
CPC .... *A61B 17/12145* (2013.01); *A61B 17/1204* (2013.01); *A61B 17/1215* (2013.01);
(Continued)

(58) Field of Classification Search
CPC ........ A61B 17/12022; A61B 17/12027; A61B 17/12031; A61B 17/12036;
(Continued)

(56) References Cited

U.S. PATENT DOCUMENTS

| 4,503,569 A | 3/1985 | Dotter |
| 4,606,336 A | 8/1986 | Zeluff |

(Continued)

FOREIGN PATENT DOCUMENTS

| CA | 2527976 A1 | 12/2004 |
| EP | 2098174 A2 | 9/2009 |

(Continued)

OTHER PUBLICATIONS

End. (n.d.). Dictionary.com Unabridged. Retrieved Dec. 20, 2016 from Dictionary.com website http://www.dictionary.com/browse/end.*

(Continued)

*Primary Examiner* — Kathleen S Holwerda
*Assistant Examiner* — Kankindi Rwego
(74) *Attorney, Agent, or Firm* — Dorsey & Whitney LLP

(57) ABSTRACT

An occlusion device for a vascular or biological lumen includes a plurality of coiling members held together at both the proximal and distal ends by retaining features. A restraining loop can hold coiling members together at a point along a length of the coiling members. The coiling members are delivered simultaneously to form a coil pack to occlude a target location in the lumen. One or more of the coiling members has at least a portion with a larger curl diameter than other coiling members to secure the occlusion device (Continued)

against lumen walls at the target location. The coil members may have different or varying material moduli. The device may be used, for example, for occluding a vessel to block blood flow to an artery supplying blood liver (hepatic artery), kidney (renal artery), spleen (splenic artery) or intestines (mesenteric artery).

27 Claims, 10 Drawing Sheets

(51) Int. Cl.
*A61M 39/02* (2006.01)
*A61B 17/00* (2006.01)
(52) U.S. Cl.
CPC .. *A61B 17/12031* (2013.01); *A61B 17/12104* (2013.01); *A61B 17/12109* (2013.01); *A61M 5/00* (2013.01); *A61M 39/0208* (2013.01); *A61B 2017/00526* (2013.01); *A61B 2017/00867* (2013.01); *A61B 2017/1205* (2013.01); *A61B 2017/12054* (2013.01); *A61M 2039/0232* (2013.01); *Y10T 29/49863* (2015.01)
(58) Field of Classification Search
CPC .......... A61B 17/1204; A61B 17/12099; A61B 17/12113; A61B 17/12118; A61B 17/12122; A61B 17/12131; A61B 17/1214; A61B 17/12145; A61B 17/1215; A61B 17/12154; A61B 17/12163; A61B 2017/00867; A61B 2017/1205; A61B 2017/12054; A61B 2017/12109; A61B 17/0057; A61B 17/12109; A61B 17/12159; A61B 17/1268; A61B 17/12172; A61F 2/01; A61F 2/013; A61F 2002/011; A61F 2002/015; A61F 2002/016; A61F 2002/018
See application file for complete search history.

(56) References Cited

U.S. PATENT DOCUMENTS

| | | | |
|---|---|---|---|
| 4,950,258 A | 8/1990 | Kawai et al. | |
| 4,994,069 A | 2/1991 | Ritchart et al. | |
| 5,163,952 A | 11/1992 | Froix | |
| 5,258,020 A | 11/1993 | Froix | |
| 5,599,291 A | 2/1997 | Balbierz et al. | |
| 5,603,722 A | 2/1997 | Phan et al. | |
| 5,649,949 A | 7/1997 | Wallace et al. | |
| 5,674,242 A | 10/1997 | Phan et al. | |
| 5,733,294 A * | 3/1998 | Forber | A61B 17/12022 |
| | | | 606/151 |
| 5,800,455 A | 9/1998 | Palermo et al. | |
| 5,830,230 A | 11/1998 | Berryman et al. | |
| 5,911,717 A * | 6/1999 | Jacobsen | A61B 17/12022 |
| | | | 606/1 |
| 5,964,744 A | 10/1999 | Balbierz | |
| 6,086,577 A | 7/2000 | Ken | |
| 6,090,125 A | 7/2000 | Horton | |
| 6,160,084 A | 12/2000 | Langer et al. | |
| 6,165,198 A | 12/2000 | McGurk et al. | |
| 6,221,066 B1 | 4/2001 | Ferrera et al. | |
| 6,248,129 B1 | 6/2001 | Froix | |
| 6,281,262 B1 | 8/2001 | Shikinami | |
| 6,355,052 B1 * | 3/2002 | Neuss | A61B 17/0057 |
| | | | 606/213 |
| 6,368,356 B1 | 4/2002 | Zhong et al. | |
| 6,383,204 B1 | 5/2002 | Ferrera | |
| 6,388,043 B1 | 5/2002 | Langer et al. | |
| 6,550,480 B2 | 4/2003 | Feldman et al. | |
| 6,551,305 B2 | 4/2003 | Ferrera et al. | |
| 6,554,849 B1 | 4/2003 | Jones et al. | |
| 6,616,617 B1 | 9/2003 | Ferrera et al. | |
| 6,712,810 B2 | 3/2004 | Harrington et al. | |
| 6,720,402 B2 | 4/2004 | Langer et al. | |
| 6,740,094 B2 | 5/2004 | Maitland et al. | |
| 6,746,461 B2 | 6/2004 | Fry | |
| 6,887,266 B2 | 5/2005 | Williams et al. | |
| 7,115,691 B2 | 10/2006 | Alvarado et al. | |
| 7,208,550 B2 | 4/2007 | Mather et al. | |
| 7,217,744 B2 | 5/2007 | Lendlein et al. | |
| 7,611,524 B1 | 11/2009 | Maitland et al. | |
| 2002/0016613 A1 | 2/2002 | Kurz et al. | |
| 2002/0052613 A1 | 5/2002 | Ferrra et al. | |
| 2002/0161397 A1 | 10/2002 | Mathews et al. | |
| 2002/0173839 A1 | 11/2002 | Leopold et al. | |
| 2003/0066533 A1 | 4/2003 | Loy | |
| 2003/0083735 A1 | 5/2003 | Denardo et al. | |
| 2003/0149470 A1 | 8/2003 | Alvarado et al. | |
| 2003/0199919 A1 | 10/2003 | Palmer et al. | |
| 2004/0030062 A1 | 2/2004 | Mather | |
| 2004/0122174 A1 | 6/2004 | Mather et al. | |
| 2004/0193246 A1 | 9/2004 | Ferrera | |
| 2005/0021074 A1 | 1/2005 | Elliott | |
| 2005/0033163 A1 | 2/2005 | Duchon et al. | |
| 2005/0038460 A1 | 2/2005 | Jayaraman | |
| 2005/0085847 A1 * | 4/2005 | Galdonik | A61F 2/01 |
| | | | 606/200 |
| 2005/0171572 A1 | 8/2005 | Martinez | |
| 2005/0212630 A1 | 9/2005 | Buckley | |
| 2005/0234540 A1 | 10/2005 | Peavey et al. | |
| 2005/0273135 A1 * | 12/2005 | Chanduszko | A61B 17/0057 |
| | | | 606/213 |
| 2006/0030933 A1 | 2/2006 | DeLegge et al. | |
| 2006/0036045 A1 | 2/2006 | Wilson et al. | |
| 2006/0041089 A1 | 2/2006 | Mather et al. | |
| 2006/0079926 A1 | 4/2006 | Desai et al. | |
| 2006/0095134 A1 | 5/2006 | Trieu et al. | |
| 2006/0129232 A1 | 6/2006 | Dicarlo et al. | |
| 2006/0142794 A1 | 6/2006 | Lendlein et al. | |
| 2006/0206140 A1 | 9/2006 | Shaolian et al. | |
| 2006/0213522 A1 | 9/2006 | Menchaca et al. | |
| 2006/0241682 A1 | 10/2006 | Kurz | |
| 2006/0241686 A1 | 10/2006 | Ferrera et al. | |
| 2006/0280768 A1 | 12/2006 | Hwang et al. | |
| 2007/0016233 A1 | 1/2007 | Ferrera et al. | |
| 2007/0083226 A1 | 4/2007 | Buiser et al. | |
| 2007/0141339 A1 | 6/2007 | Song et al. | |
| 2007/0142893 A1 | 6/2007 | Buiser et al. | |
| 2007/0233037 A1 | 10/2007 | Gifford et al. | |
| 2007/0250081 A1 * | 10/2007 | Cahill | A61B 17/0057 |
| | | | 606/151 |
| 2008/0004692 A1 | 1/2008 | Henson | |
| 2008/0082176 A1 | 4/2008 | Slazas | |
| 2008/0086217 A1 * | 4/2008 | Jones | A61B 17/12022 |
| | | | 623/23.76 |
| 2008/0097508 A1 | 4/2008 | Jones et al. | |
| 2008/0114391 A1 | 5/2008 | Dieck et al. | |
| 2008/0147111 A1 | 6/2008 | Johnson et al. | |
| 2008/0195139 A1 | 8/2008 | Donald et al. | |
| 2008/0281405 A1 | 11/2008 | Williams et al. | |
| 2008/0312733 A1 | 12/2008 | Jordan | |
| 2009/0056722 A1 | 3/2009 | Swann | |
| 2009/0099647 A1 | 4/2009 | Gimsdale et al. | |
| 2009/0112251 A1 | 4/2009 | Qian et al. | |
| 2010/0262177 A1 * | 10/2010 | Frigstad | A61B 17/12022 |
| | | | 606/191 |
| 2011/0184452 A1 | 7/2011 | Huynh et al. | |
| 2011/0196487 A1 | 8/2011 | Badawi et al. | |

FOREIGN PATENT DOCUMENTS

| | | |
|---|---|---|
| JP | H1024039 A | 1/1998 |
| JP | 2001520085 A | 10/2001 |
| WO | 94/06503 A1 | 3/1994 |
| WO | 00/62711 A1 | 10/2000 |
| WO | 2004110313 A1 | 12/2004 |
| WO | 2008/051254 A1 | 5/2008 |

(56) References Cited

FOREIGN PATENT DOCUMENTS

| WO | 2010/135352 A1 | 11/2010 | | |
|---|---|---|---|---|
| WO | 2011084536 A2 | 7/2011 | | |
| WO | WO-2011084536 A2 * | 7/2011 | ....... | A61B 17/12022 |

OTHER PUBLICATIONS

Author Unknown, "0.18 and 0.035 Fibered Platinum Coils", Boston Scientific (www.bostonscientific.com), accessed at least as early as Jan. 2010, pp. 1.

Author Unknown, ,"Brain Aneurysm Treatment", Boston Scientific (www.bostonscientific.com), accessed at least as early as Jan. 2010, pp. 2.

Author Unknown, "Matrix2 Detachable Coils, Occlusion is only the beginning . . . ", Boston Scientific (www.bostonscientific.com), accessed at least as early as Jan. 2010, pp. 1-8.

Author Unknown, "Neurovascular Intervention", Boston Scientific (www.bostonscientific.com), accessed at least as early as Jan. 2010, pp. 2.

Author Unknown, "Shape Memory Therapeutics Receives Texas Emerging Technology Fund Award", Biomedical Engineering, Texas A&M University, Oct. 21, 2009, pp. 2.

Author Unknown, "VortX 18 and 35 Vascular Occlusion Coils", Boston Scientific (www.bostonscientific.com), accessed at least as early as Jan. 2010, pp. 2.

Codman & Shurtleff, Inc., , "Trufill DCS Orbit Detachable Coil System", http://www.codman.com/DePuy/products/Products/neurovascular/trufillorbit/index.html, accessed at least as early as Jan. 2010.

De Nardo, Luigi et al., "Shape memory polymer foams for cerebral aneurysm reparation: Effects of plasma sterilization on physical properties and cytocompatibility", www.sciencedirect.com, ActaBioMaterialia, 2009, pp. 1508-1518.

EV3 Inc. "Embolic Coils", ev3 Inc., http://www.ev3.net/neuro/intl/embolic-coils/nxt-detachable-coils5391.htm, accessed at least as early as Jan. 2010, pp. 1.

Gall, Ken et al., "Thermomechanics of the Shape Memory effect in polymers for biomedical applications", J. Biomed Mater Res 73A, 2005; 73(3): 339-348, Apr. 1, 2005 (www.interscience.wiley.com) Wiley Int Science, (2005).

Hampikian, Janet M. et al., "Mechanical and radiographic properties of a shape memory polymer composite for intracranial aneurysm coils", Materials Science and Engineering C 26, (2006), pp. 1373-1379.

Heaton, Brian C. , "A Shape Memory Polymer for Intracranial Aneurysm Coils: An Investigation of Mechanical and Radiographic Properties of a Tantalum-Filled Shape Memory Polymer Composite", Georgia Institute of Technology, Jul. 2004, pp. 1-60.

Maitland, D. J. et al., "Photothermal properties of shape memory polymer micro-actuators for treating stroke", Las. Surg. Med., vol. 30, No. 1, 2002, pp. 1-11.

Maitland, Duncan J. et al., "Design and Realization of Biomedical Devices Based on Shape Memory Polymers", Materials Research Society, Spring 2009.

Maitland, Duncan J. et al, "Prototype laser-activated shape memory polymer foam device for embolic treatment of aneurysms", Journal of Biomedical Optics, May/Jun. 2007, vol. 12(3), pp. 030504-1-3.

Metzger, M. F. et al., "Mechanical properties of mechanical actuator for treating ischemic stroke", Biomed. Microdevices, vol. 4, No. 2, 2002, Nov. 2, 2002, pp. 89-96.

Microvention Terumo, , "HydroSoft", http://www.microvention.com/Products/Coils/HydrogelProducts/HydroSoft/tabid/70/default.aspx, accessed at least as early as Jun. 8, 2010, pp. 2.

Microvention Terumo, "MicroPlex Coil System", http://www.microvention.com/Products/Coils/MicroPlexProducts/tabid/63/default.aspx, accessed at least as early as Jun. 8, 2010, pp. 1.

Microvention Terumo, , "The Facts About HydroCoil", http://www.microvention.com/Products/Coils/HydrogelProducts/HydroCoil/tabid/69/Default.aspx, accessed at least as early as Jun. 8, 2010, pp. 2, 1-2.

Micrus Endovascular, , "Enhanced Embolic Coils for the Treatment of Cerebral Aneurysms", http://www.micrusendovascular.com/products/cerebyte_intl.asp?ln=h, accessed at least as early as Jan. 2010, pp. 3.

Neurovasx, "ePAX", http://www.neurovasx.com, accessed at least as early as Jan. 2010, pp. 1.

Prosecution Document, "Japan Office Action", Japanese Office Action dated Jun. 3, 2014 for Japanese Patent Application No. 2012-544799, 5 pages.

Small, IV, Ward et al., "Biomedical applications of thermally activated shape memory polymers", J. Mater. Chem., 2010, 20, Mar. 2, 2010, Mar. 2, 2010, pp. 3356-3366.

University of California, Davis , "Development of aneurysm treatment using laser-deployed shape memory polymer foams", http://cbst.ucdavis.edu/research/aneurysm-treatment/development-of-aneurysm-treatment-using-laser-deployed-shape-memory-polymer-foams, accessed at least as early as 2007, 3 pages.

Wilson, Thomas S. et al., "Shape Memory Polymer Therapeutic Devices for Stroke", Smart Medical and Biomedical Senso Technology, III, Proc. of SPIE, vol. 6007 (2005), pp. 60070R-1-8.

Yakacki, Christopher J. et al., "Optimizing the thermomechanics of shape-memory polymers for biomedical applications", Material Research Society Symposium Proceedings, vol. 855E, Dec. 1, 2004, pp. 106-111.

Japanese Office Action for Japanese Patent Application No. 2014-552404, dated Dec. 13, 2016 (10 pages).

* cited by examiner

OCCLUSION DEVICE FOR A VASCULAR OR BIOLOGICAL LUMEN

CROSS REFERENCE TO RELATED APPLICATIONS

The present application claims the benefit of priority under 35 USC § 119(e) to U.S. Patent Application No. 61/587,518 filed 17 Jan. 2012 entitled "Occlusion Device for a Vascular or Biological Lumen" and to U.S. Patent Application No. 61/641,145 filed 1 May 2012 entitled "Occlusion Device for a Vascular or Biological Lumen" each of which is hereby incorporated herein by reference in its entirety.

The present application is also related to U.S. Patent Application No. 61/591,119 filed 26 Jan. 2012 entitled "Delivery Apparatus for Distal and Proximal Control of Lumen Occlusion Device and Patent Cooperation Treaty Application No. PCT/US2010/060598 filed 15 Dec. 2010 entitled "Multi-fiber shape memory device" and Patent Cooperation Treaty Application No. PCT/US2010/029742 filed 2 Apr. 2010, entitled "Vascular occlusion devices" each of which is hereby incorporated herein by reference in its entirety.

STATEMENT REGARDING FEDERALLY SPONSORED RESEARCH OR DEVELOPMENT

This technology was developed in part with sponsorship by National Science Foundation Grant No. 0823015 and the U.S. federal government may have certain rights to this technology.

TECHNICAL FIELD

The invention relates generally to implantable devices for therapeutic treatment, and more particularly relates to an endoluminally delivered device for occlusion of a vascular or biological lumen.

BACKGROUND

During many clinical procedures, a physician requires the reduction or complete stoppage of blood flow to a target region of the patient's body to achieve therapeutic benefit. A variety of devices are available to provide occlusion of blood vasculature including: embolic coils, metal-mesh vascular plugs, beads, particles and glues. From this selection, interventional radiologists and vascular surgeons (and similar medical specialists) draw from these choices based upon the specific need and confidence of a rapid and effective occlusion given the attributes and deficiencies of each of these options. These devices may be used to occlude vasculature in situations, for example, requiring treatment of arteriovenous malformations (AVMs), traumatic fistulae, some aneurysm repair, uterine fibroid and tumor embolization. For these clinical treatments, the blood flow through a target section of a blood vessel must be stopped. The device is introduced into the blood vessel through a sterile delivery catheter or sheath using common percutaneous access outside the body. The delivered, artificial device, induces an initial reduction of blood flow through a simple mechanical blockage which in turn triggers the body's natural clotting process to form a more complete blockage comprised of the thrombus adhered to the device.

Current exemplary embolic coils are made from biocompatible materials and provide a biodurable, stable blockage of blood flow. The coils anchor to the vessel wall through radial compliance pressing onto the vessel wall surface. Coils must be suitably anchored to avoid migrating downstream under the forces of the blood flow, which can be significant in larger vasculature. Embolic coils are often shaped for flexibility through a primary coiling and for achieving a "coil pack" within the vessel through a secondary, sometimes complex, three dimensional shape. The coil pack appears as a relatively random crossing and intertwining of the coil within the vessel. After slowing the blood flow, over time, a clot forms around the embolic coil, and blood flow through the section is completely blocked.

Typical embolic coils are formed using two major steps: 1) a wire of platinum or other bio-compatible material is wound into a spring, forming what is commonly referred to as a primary coil; and 2) the primary coil is in turn wound around a mandrel having a more complex shape and is subject to high heat to yield a secondary coil. The secondary coil thus is a coiled wire of complex-shape or if helical, a larger curl diameter. Coils can also be provided in multiple secondary shapes including multiple helical curl diameters and in tapered helical shapes with one end employing a large curl diameter and the other end a small curl diameter. These metal coils are straightened, within their elastic bending limit, so as to be advanced into a delivery catheter and pushed down the catheter by a guide wire, pusher, or a detachable pre-attached pusher, until expelled into the vessel. Often, polymeric fibers are applied to the metallic coils in order to increase a thrombus response in addition to providing a scaffolding for thrombus to adhere to and be retained on the coil.

Embolic coils are sized to fit within the inner lumen of a catheter or sheath to be delivered to the target occlusion site individually and sequentially. Typically, a physician will use multiple coils to occlude a single vessel and in some cases, especially for larger blood vessels (above 5 mm or so), the physician may use a significant number of coils to achieve cessation of blood flow. To complete an occlusion procedure with embolic coils, the physician must sequentially reload the catheter with several individual coils until he/she has determined the occlusion is sufficient. The physician typically determines whether sufficient coils have been deployed by assessing the level of occlusion of the vessel flow by using contrast media in concert with typical medical imaging techniques. This "place and assess" method can extend the medical procedure time, expose the patient to increased levels of contrast agent, and increase radiation exposure to both the patient and the physician through extensive imaging. A singular device that achieves vascular occlusion with one application would overcome these coil limitations.

Embolic coils are also known for challenges in achieving precise vascular placement. Many of these coils are simply pushed out of the end of a delivery catheter. The final coil pack location is dependent upon whether the coil has been properly sized prior to deployment, or whether the coil was properly anchored into a side vessel/branch as prescribed by several of the coil manufacturers for greater confidence in the coil packs final position. Both of these technique issues require a high level of physician skill if there is a desire to accurate position both the distal and proximal faces of the coil pack in a vessel using sequential, pushable coils. Some of the coil manufacturers provide a detachable coil wherein at the user's discretion a placed coil can be released from a delivery control wire. If the coil is not in the preferred location, it can be retracted and replaced if needed to achieve better position. However, only the proximal end of the coil is attached to this control wire resulting in only indirect control of the position of the coil pack's distal face.

Using coils for embolization can present unique challenges. Voids in the coil pack, developed either during the procedure or post operatively, can cause channels and resulting blood flow in an unintended area. This condition is typically referred to as recanalization. Depending upon the significance of the condition, e.g., an internal hemorrhage, re-treatment or surgical intervention may be necessary. The ability to quickly and reliably develop a consistent coil pack in a vessel is important for a successful vascular occlusion product.

Also, embolic coils can be easily misplaced. Embolic coils may either be injected through a delivery catheter with a syringe filled with saline, pushed by an independent guide wire, or deployed with a detachable pusher that is only connected to the coil via its proximal end. The coil pack shape is dependent upon the successful placement of the initial coil. Therefore coils can easily be misplaced should the initial coil not land correctly or be slightly undersized to the target vessel and slip beyond the target location. As such, embolic coil packs are known for a high propensity of being elongated in overall size. While clinically accepted, coils reflect significant challenges when attempting to embolize in a very precise or limited section of vasculature.

Metal mesh vascular plug devices have also been developed and commercialized to achieve vascular occlusion. These devices achieve occlusion with a single deployment using a metal mesh to provide mechanical flow blockage and, after some time, thrombus forms and a complete occlusion results. When deployed, these devices appear like metal mesh balloons or baskets, with one or more lobes contacting the vascular wall, but with defined proximal and distal faces. With occlusion occurring after a single device deployment, these products address many of the deficiencies of embolic coils. However, due to the porosity of the mesh basket and the lack of the polymeric fibers used in coils, the metal mesh plugs have been shown to take longer to achieve occlusion than a properly placed embolic coil pack.

Further, these metal mesh devices are relatively stiff due to their construction and have limited ability to traverse sharp turns found in catheters that have been placed in a highly tortuous vascular path. The mesh is collapsed into a narrow tube-like shape for introduction and deployment through a delivery catheter or sheath before expanding into the balloon-like shape upon deployment. This narrow tube-like shape allows the device to be delivered in the central lumen of small catheters or sheaths similar to coils. However, when the mesh is collapsed, it elongates and becomes a fairly rigid tubular structure. So, while being capable of entry into a small delivery catheter it has limited ability to traverse sharp turns found in catheters that have been placed in a highly tortuous path to reach the target vessel for occlusion. Subsequently, the advantages of a single occlusion device are offset by the slow occlusion performance and limited application to occlusion target sites that are less tortuous to access.

The information included in this Background section of the specification, including any references cited herein and any description or discussion thereof, is included for technical reference purposes only and is not to be regarded subject matter by which the scope of invention is to be bound.

SUMMARY

As described herein, the vascular or biological lumen occlusion device may be configured as a set of parallel elongated coiling members joined at their respective ends by a retaining feature. That is, the proximal ends of the individual coiling members are joined or otherwise held together by a retaining feature and the distal ends of the individual coiling members are joined or held together by a retaining feature. Joining the coiling members at the distal end provides greater positional control of the resulting coil pack for vessel occlusion (e.g., a vascular or other biological lumen vessel), reduces the potential for errant coiling members to extend downstream (distal) in the vessel and facilitates the ability to incorporate a detachable distal control wire that will help to guide the coiling members into proper placement within the vessel. Joining multiple coiling members at both a proximal and distal ends is unique for vessel occlusion products, and particularly vascular occlusion products. In some implementations, individual elongate coiling members may also have a unique curl design and material properties to facilitate anchoring the device within the vessel and to tightly pack the device in the vessel to minimize occlusion time.

The disclosed device may be similarly beneficial regardless of material employed for the coiling members, e.g., metals (stainless, platinum, Nitinol), traditional polymers/plastics (thermoplastic or thermoset resins), shape memory polymers, or a combination of these. The disclosed device may be similarly beneficial with one or more of the features in unique combination, e.g., straight coiling members with a distal control wire, helical coiling members with a restraining loop, all coiling members using the same curl diameter and material modulus, etc.

In one aspect, a vascular or biological lumen occlusion device for occluding a target is disclosed. The occlusion device includes a plurality of coil members having varying curl diameters, each member having a proximal end and a distal end. The device also includes a proximal retaining feature coupled to the proximal ends of the plurality of coil members and a distal retaining feature coupled to the distal ends of the plurality of coil members. The retaining features may be a homogenous section formed by either the coil material or by an adhesive, solder, or other joining agent. In some embodiments, the plurality of coiling members have varying curl diameters.

In one aspect, a first coiling member of the plurality of coil members defines a first curl diameter. A second coiling member of the plurality of coil members defines a second curl diameter that is smaller than the first curl diameter. The first coiling member is configured to anchor the device in the target location and the second coiling member is configured to fill the target location by creating a dense coil pack.

In one aspect, a first coiling member of the plurality of coiling members defines a first portion having a first curl diameter and a second portion having a second curl diameter that is smaller than the first curl diameter. The first portion of the first coiling member is configured to anchor the lumen occlusion device in the target location. Further, the plurality of coiling members are configured to fill the target location by creating a dense coil pack.

In one implementation the device may further include at least one restraining loop coupled to at least one of the plurality of coiling members along a length of the coiling members. In one implementation, the device may further include an engagement feature integrally formed with the distal retaining feature, said engagement feature configured to also engage the proximal retaining feature to enhance the radial expansion of the coil pack by encouraging a compressed stable axial dimension. In one implementation the proximal retaining feature defines an aperture and the engagement feature is a tubular body extending proximally from the distal retaining feature and includes detents configured to engage an inner circumference of the aperture of the proximal retaining feature. In another implementation a hook-like feature is integrally formed with the proximal retaining feature and the engagement feature is an opening in the distal retaining feature, said opening configured to receive the hook-like feature. In one implementation the plurality of coil members are shape memory polymers. In one implementation, the first coiling member has a first material modulus and the second coiling member has a second material modulus. In one implementation, the second material modulus is less than the first material modulus. In one implementation, the first portion has a first material modulus and the second portion has a second material modulus. In one implementation, the coiling members are made from radiopaque polymers, radiopaque crosslinked, thermoset polymers, or radiopaque shape memory polymers. In one implementation, the first curl diameter is between approximately 12 mm and approximately 8 mm. In one implementation, the second curl diameter is between approximately 9 mm and approximately 6 mm. In one implementation, each of the coiling members has a coil diameter of approximately 0.018 inches. In one implementation, the first member of the plurality of coiling members further includes a third curl diameter that is smaller than the first curl diameter. In one aspect, the second member of the plurality of coiling members further includes a fourth curl diameter that is smaller than the second curl diameter. In one implementation, the device further includes nylon fibers coupled to one or more of the plurality of coiling members to promote thrombus formation. In one aspect, a vascular or biological lumen defines a lumen diameter and the first curl diameter is between approximately 20% and approximately 70% greater than the lumen diameter. In one implementation, the second curl diameter is less than the lumen diameter.

In one aspect, a method of manufacturing a vascular or biological lumen occlusion device is disclosed. In one implementation, the method includes providing a plurality of flexible bodies. A plurality of coiled members is formed from the plurality of flexible bodies according to methods as disclosed herein. The plurality of coiled members are constrained in a pre-deployed state as a plurality of elongate members, each of the plurality of elongate members having a proximal end and a distal end. In one implementation the method further includes coupling the distal ends of the plurality of elongate members with a distal retaining feature. The method may also include coupling the proximal ends of the plurality of elongate members with a proximal retaining feature. The method may further include forming a first coiling member of the plurality of coiled members to have a first curl diameter between 20% and 70% greater than a target lumen diameter and a first material modulus. The method may further include forming a second coiled member of the plurality of coiled members with a second curl diameter smaller than the target lumen diameter and a second material modulus. The method may further include providing a delivery device having a pusher mechanism and a detachment feature, and operably attaching the distal retaining feature to the detachment feature. In one implementation, the method may further include coupling the plurality of elongate members with a retaining loop. The method may further include coupling nylon fibers to a portion of one or more of the plurality of elongate members to promote thrombus formation.

In another aspect, a method of occluding a vascular or biological lumen is disclosed. In one implementation, the method includes introducing a lumen occlusion device preloaded in a delivery device to a target location. The occlusion device includes a plurality of coiling members, each member having a proximal end and a distal end. The device further includes a proximal retaining feature coupled to the proximal ends of the plurality of coiling members and a distal retaining feature coupled to the distal ends of the plurality of coiling members. The method further includes deploying the occlusion device at the target location. In one implementation, a first member of the plurality of coiling members has a first curl diameter and a first material modulus and a second member of the plurality of coiling members has a second curl diameter and a second material modulus. The method further includes deploying the occlusion device at the target location such that the first coiling member is configured to anchor the device in the target location and the second coiling member is configured to fill the target location by creating a dense coil pack.

In one implementation, the occlusion device further includes a detachment feature coupled to the distal retaining feature, and the deploying operation further comprises releasing the detachment feature from the delivery device. In one implementation, the method further includes positioning the occlusion device by advancing the detachment feature past a distal end of the delivery device to a position in the target location that will result in the occlusion device forming a dense coil pack. In one implementation, the method further includes disengaging at least a portion of the detachment feature from the distal retaining feature and retracting the portion of the detachment feature back into the delivery device without removing the coil pack. In one implementation, the method further includes the lumen occlusion device in a peripheral vessel thereby occluding the peripheral vessel for treatment of uterine fibroids, varicoceles or internal hemorrhage. In one implementation, the method further includes placing the lumen occlusion device in a peripheral artery thereby occluding the peripheral artery before undertaking other procedures including one or more of placing a port or injecting a chemotherapy agent. In one implementation, the method further includes placing the lumen occlusion device in a biological lumen selected from the group consisting of a fallopian tube, a lung lobe, or a bile duct.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 3A-2 illustrates the varying curl sizes of the coiling member of FIG. 3A-1.

FIG. 3A-3 depicts the coiling member of FIG. 3A-1 in an elongated state (a pre-deployed or stored shape).

FIG. 3B-1 depicts an exemplary embodiment of a second coiling member shown in FIG. 2.

FIG. 3B-2 illustrates the varying curl sizes of the coiling member of FIG. 3B-1.

FIG. 3B-3 depicts the coiling member of FIG. 3B-1 in an elongated state (a pre-deployed or stored shape).

FIG. 4A-1 depicts still another exemplary embodiment of a coiling member of the device of FIG. 1A, wherein the coiling member is shown in a resting state after removal from a winding mandrel.

FIG. 4A-2 illustrates the coiling member of FIG. 4A-1 in an expanded (non-relaxed) state.

DETAILED DESCRIPTION

Figure 1A:
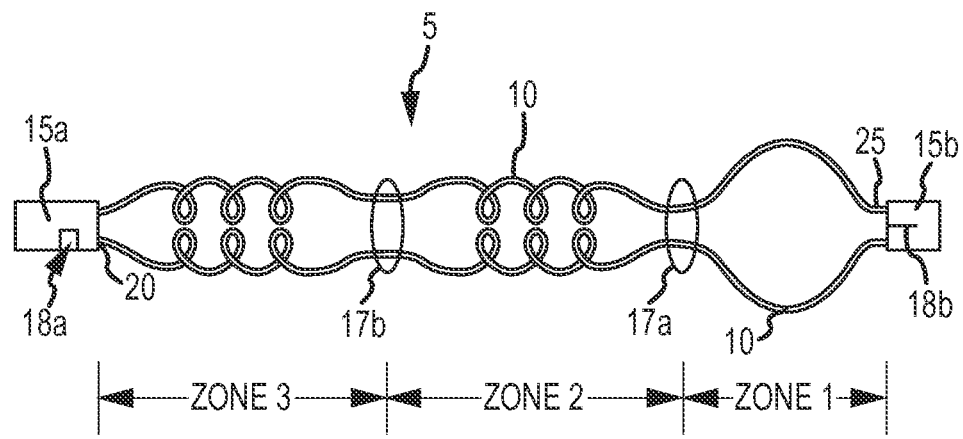
FIG. 1A is a depiction of a lumen occlusion device having coiling members and retaining features shown in a displayed state, wherein functional zones of the device are also shown.

The target anatomy for vascular occlusion (e.g., internal hemorrhage, tumor isolation, aneurysms, AVMs, etc.) present significant anatomical variability and in many cases, accessing this target anatomy requires a significantly tortuous vascular path in which the delivery catheter or delivery sheath has been placed by a physician, such as an interventional radiologist, prior to deployment of the occlusion device. Other biological lumens, such as fallopian tubes, lung lobes (e.g., for a resection), bile ducts, etc. may also present similar anatomical variability and, accordingly, tortuous delivery paths. The occlusion device enters the delivery catheter outside the patient's body and travels down the delivery catheter or delivery sheath to be deployed (expelled) into the target vessel location. At that point, the device is intended to change shape and expand so as to occlude the vessel. Therefore, a clinically acceptable occlusion device is flexible to translate down the catheter and adaptive to the structure it is filling. Further, the device will anchor to the vessel wall to resist migration from the influence of the lumen flow, e.g., blood, air, bile, etc.

Disclosed herein is a lumen occlusion device having multiple parallel elongate, coiling members (e.g., stands, strings, wires, fibers, threads, etc.), retaining features and a restraining loops, wherein the multiple elongate coiling members are delivered in parallel and simultaneously as one unique device to form a coil pack to occlude a vascular target (or other biological lumen target) upon deployment from a delivery sheath. The occlusion device may be used, for example, for occluding an artery or vein, to block blood flow within a vessel supplying blood to or from the liver (hepatic artery), kidney (renal artery), spleen (splenic artery) or intestines (mesenteric artery). Other applications may include use in other biological lumens such as the fallopian tubes, the lung lobes (e.g., for a resection), bile ducts or etc. Applications of the occlusion device are not limited to specific vessels but wherever in the body that a physician desires to use catheter delivered lumen occlusion as part of the patient's therapeutic treatment. In one exemplary application, the gastroduodenal artery (GDA) is embolized prior to insertion of a port for administering chemotherapy agents in support of oncology treatment for liver cancer. A quick and simple way to occlude the GDA is highly beneficial to the physician as occlusion is a supportive task of the patient's therapy, not the primary task.

With individual embolic coils, physicians may experience distal "prolapse" or proximal "bucking" or "recoil" that describe errant coil behavior. When one or more loops of coils extend distal of the target vascular site, the device has prolapsed and, if it can't be retracted during deployment, it may be left in a non-optimal location (if not deemed hazardous) or it may require separate recovery via a snare or other retrieval device. When a loop of coil, in contact with a incomplete coil pack, pushes back on the catheter as reactive force opposing the deployment force, it can cause the catheter to "buck" or "recoil" unintentionally moving the catheter proximal to the coil pack. Significant catheter movement can result in misplacement of the occlusion device. Again, a snare or other retrieval device may be required if the occlusion device is left in an undesirable location, such as a parent vessel when only the branch is intended to be occluded.

In one aspect, the device is constructed as a set of parallel, elongate, coiling members joined at their respective ends by a retaining feature. That is, the proximal ends of the individual coiling members are joined or otherwise held together by a retaining feature and the distal ends of the individual coiling members are joined or held together by a retaining feature. Joining the coil members at the distal end provides greater positional control of the resulting coil pack for vascular occlusion, reduces the potential for errant coiling members to extend downstream in the vessel and facilitates the ability to incorporate a detachable distal control wire that will help to guide the coiling members into proper placement. Joining multiple members at only the proximal end was described in PCT/US2010/060598 and that configuration is very advantageous for aneurysm repair wherein the multiple members are to fill the aneurysm sack and conform to a non-symmetrical shape without placing excessive force on the diseased vessel wall. Joining multiple coiling members at both a proximal and distal ends is unique for occluding vessels or biological lumens.

The coiling members of the occlusion device may be joined together at the distal end to provide greater control of the resulting coil pack, reduce the potential for errant coils to extend downstream in the vessel, and facilitate the ability to utilize a distal control wire. The distal retaining feature may be releasably coupled to the distal control wire until the point of release, allowing for controlling the distal retaining feature during delivery of the vascular occlusion device through the delivery sheath and deployment within the vessel. The coiling members of the occlusion device may be joined together at the proximal end to provide greater control of the device during delivery, greater control of the resulting coil pack, reduce the potential for errant coils to prolapse upstream adjacent to the sheath in the vessel, and facilitate the ability to utilize a pusher that is releasably coupled to the proximal end of the occlusion device. The proximal retaining feature may be releasably coupled to the pusher that pushes the proximal retaining feature through the sheath. For a more detailed discussion of the vascular or biological lumen occlusion device, reference is first made to FIGS. 1 to 6, which illustrate various aspects of the occlusion device 5 including coil or coiling members 10, retaining features 15 and one or more restraining loops 17.

As can be understood from FIG. 1A, the implanted occlusion device 5 includes a plurality of elongate coiling members 10 which are joined at their respective proximal ends 20 and distal ends 25 by a retaining feature 15a, 15b. The retaining feature 15 may be made from the same material as the coiling members, or an adhesive, or solder, or a tubing section or crimp that compresses the ends together. In some embodiments, the retaining feature 15 may be a nubbin (e.g., a homogenous section formed by an adhesive) or other structure that permanently joins the respective proximal and distal ends of the coiling members. With the restraining loops 17a, 17b placed along the length of the occlusion device, specific zones are defined that help to describe specific device functions. For example, Zone 1 is to facilitate anchoring against the vessel wall, while Zones 2 and 3 are to facilitate packing the coiling members to achieve a dense coil pack to maximize flow reduction.

Figure 1B:
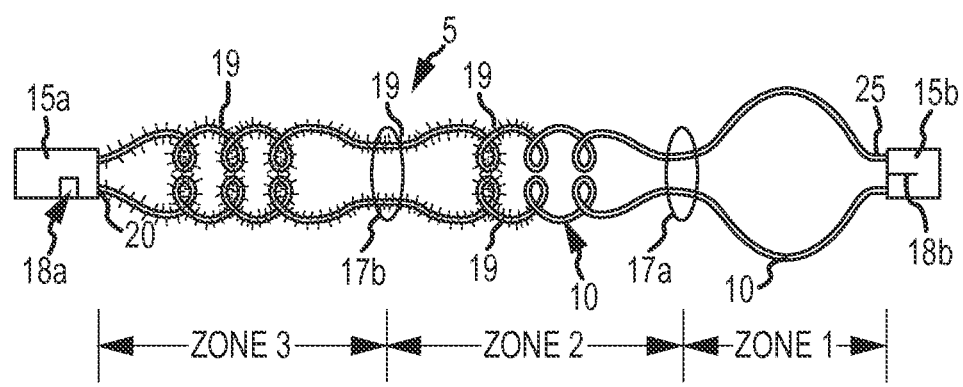
FIG. 1B depicts an exemplary embodiment of the coiling members of FIG. 1A wherein nylon fibers are coupled to portions of some of the coiling members.

In one aspect, and as shown in FIG. 1B, nylon fibers 19 may be attached to at least some of the coiling members 10. The nylon fibers encourage thrombus formation and provide a lattice for thrombus adherence to avoid releasing the thrombus downstream. As explained in more detail below, when thrombus has formed on the coil pack by adhering to the nylon fibers, complete vessel occlusion will occur.

The nylon fibers 19 may be attached or coupled to the entire length of the coiling member or may be attached to less than the entire length of the coiling member. In some embodiments, the nylon fibers may be attached to one-third, one-half or two-thirds of the length of a coiling member. In one embodiment, there are no fibers attached in approximately the distal 5 cm of the length of the coiling member. The nylon fibers 19 may be attached or coupled to at least some of the coiling members 10 in certain zones. In one embodiment having seven total coiling members, where no fibers are attached in approximately the distal 5 cm of the length of the coiling member, only five of the seven coiling members include nylon fibers. In another embodiment having seven total coiling members, where no fibers are attached in approximately the distal 5 cm of the length of the coiling member, all seven of the coiling members include nylon fibers. In one embodiment, as illustrated in FIG. 1B, the nylon fibers 19 may be coupled to the coiling members in Zone 3 and partially in Zone 2 (e.g., at a proximal end/portion of the device). Thus, one-third to one-half of the total length of the respective coiling members 10 do not have nylon fibers attached thereto.

Such a nylon fiber configuration is advantageous because it provides a practitioner additional time to confirm accurate or desired placement of the device in the vasculature. For example, during delivery (see e.g., FIGS. 8A-8F), the practitioner extends approximately one-third to one-half of the device 5 to verify the coil pack formation and position in the vasculature. If a revised placement is desired, the practitioner may withdraw/retract the device (via, e.g., the distal control wire described in co-pending U.S. Patent Application No. 61/591,119). However, during the time period where the practitioner is assessing the coil pack and placement, nylon fibers may accelerate thrombus formation. If coiling members 10 are full of thrombus, retraction may be mechanically inhibited and/or the coils may shed clots, which are both undesirable conditions. Thus, having coiling members with only partial nylon fiber coverage allows the practitioner additional time for assessment because the nylon fiber covered coil members are not immediately exposed to the vasculature. If the coil pack is acceptable and the entire device is deployed, the nylon fibers at the proximal end/portion of the coiling members will assure proper "time to occlusion" performance is achieved.

As can be understood from FIGS. 2 to 4A-2, the coiling members 10 may have any combination of varying member diameters, varying curl diameters and varying material modulus to achieve specific device functions. That is, certain coiling members may be used to facilitate expanding radially when deployed in order to provide more assurance for anchoring against the vessel wall. This is achieved by using coiling members having a larger member diameter, a larger curl diameter and a higher material modulus (e.g., stiffer). In addition, other coiling members are used to facilitate creating a dense coil pack across the vessel diameter to provide greater mechanical flow reduction which enhances thrombus formation and minimizes time to occlusion (time from deployment to when flow is stopped). This is achieved by employing coiling members having a smaller member diameter, a smaller curl diameter and a lower material modulus (e.g., softer).

In some embodiments, a set of coils may include seven individual coiling members designed to occlude a vessel of approximately 6-8 mm in diameter. In other embodiments, the set of coiling members may include fewer than seven coiling members or greater than seven coiling members to occlude a particular vessel size. In some embodiments, the number of coiling members may be 2, 3, 4, 5, 6, 8, 9, 10 or more.

Figure 2:
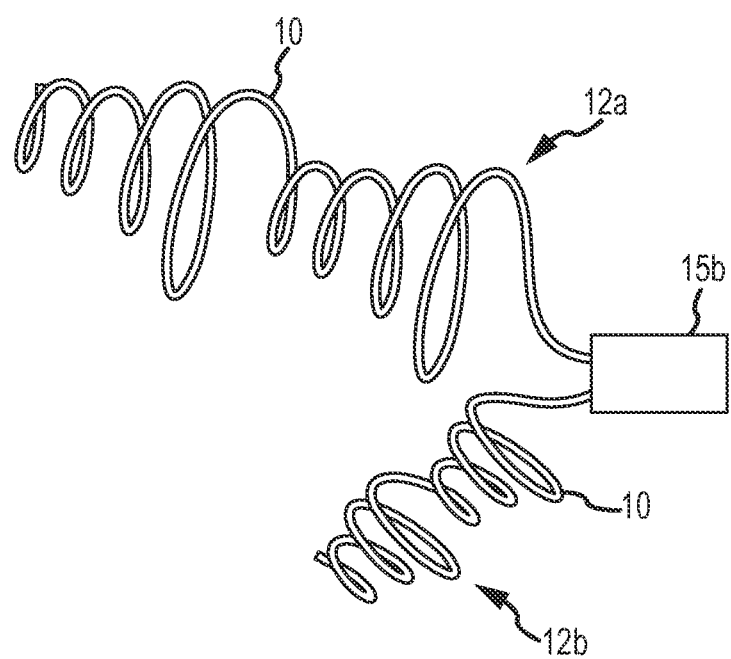
FIG. 2 illustrates an exemplary embodiment of the coiling members of FIG. 1A, wherein the coiling members have varying curl sizes.
Figures 1, 3A:
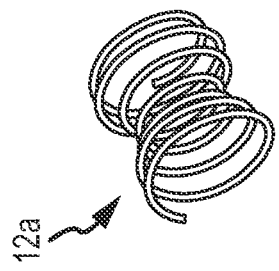
FIG. 3A-1 depicts an exemplary embodiment of a first coiling member shown in FIG. 2.
Figures 2, 3A:
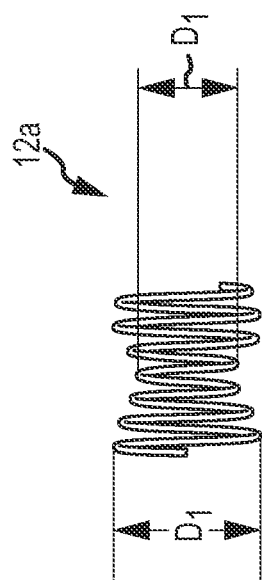
Figures 3, 3A:
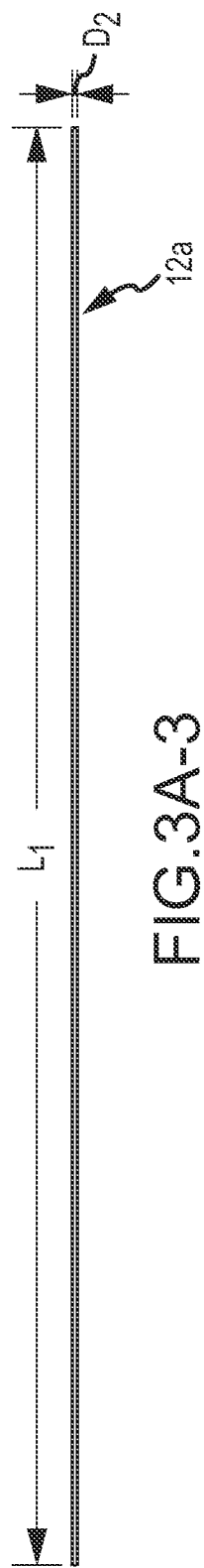
Figures 1, 3B:
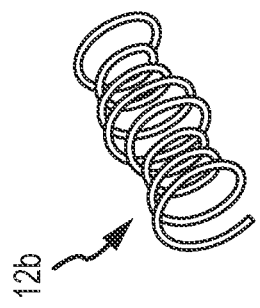
Figures 2, 3B:
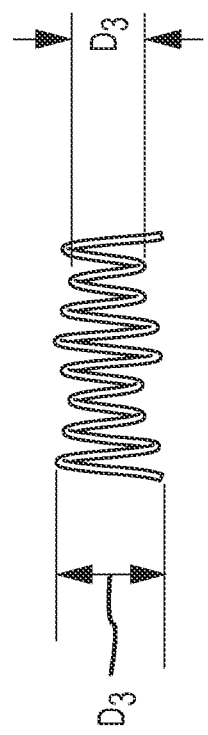
Figures 3, 3B:
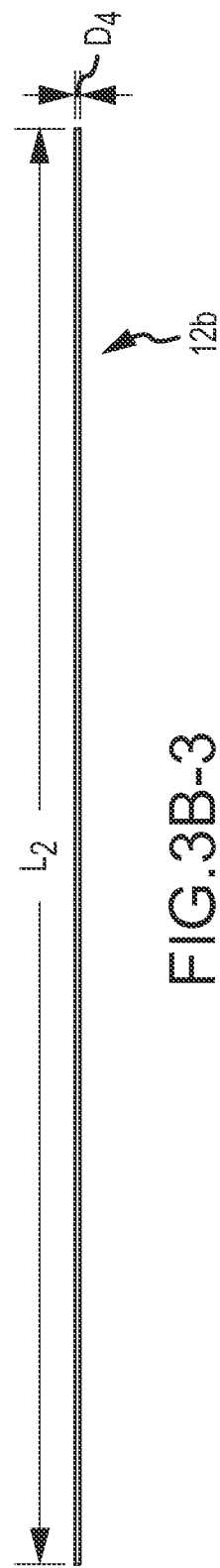
Figure 8A:
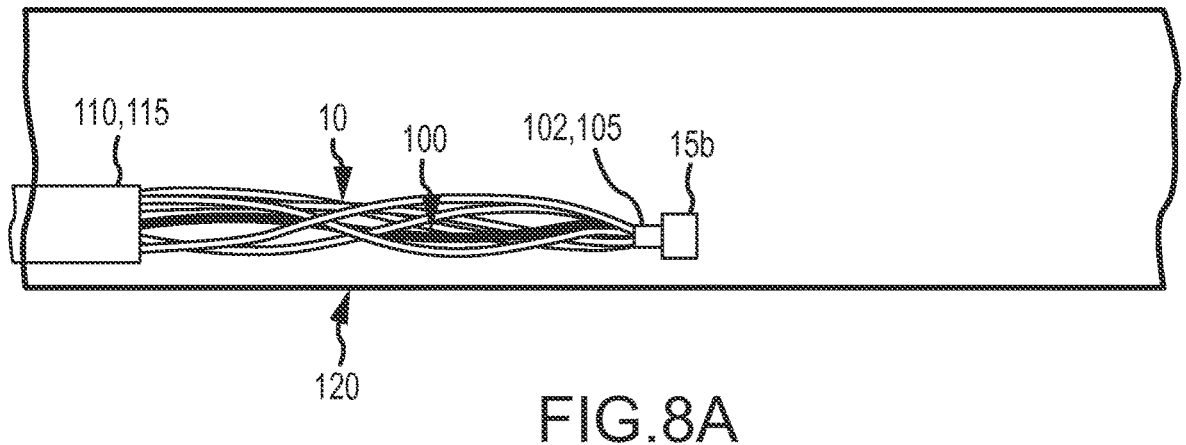
FIGS. 8A-8F depict an exemplary lumen occlusion device in the various states of deployment in accordance with the method of FIG. 7.
Figure 8B:
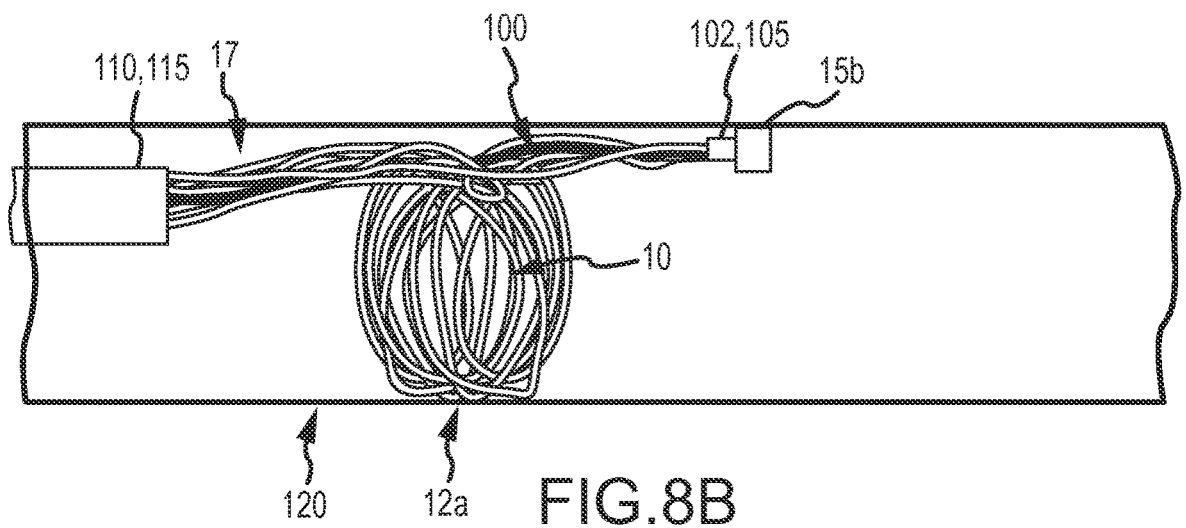

As can be understood from FIGS. 2 to 3B-3, in one embodiment, the device 5 may use seven coiling members. FIG. 2 shows an exemplary large coiling member 12a and one of the smaller coiling members 12b. In one embodiment, four coiling members may have a larger curl diameter and a higher material modulus (e.g., stiffer) (e.g., coiling member 12a). As indicated in FIG. 3A-1 and FIG. 3A-2, which show exemplary dimensions of the larger curl coiling member 12a of FIG. 2, the larger curl size may vary in diameter $D_1$ from approximately 12 mm to 8 mm. In other embodiments the curl diameter $D_1$ may vary in a range from less than approximately 8 mm to greater than approximately 12 mm. FIG. 3A-3 illustrates this larger coiling member in a pre-deployed or storage state. In one embodiment, the diameter $D_2$ of the individual coil member is approximately 0.018 mm. In other embodiments, the diameter $D_2$ of the individual coil member is between approximately 0.016 mm and 0.020 mm. In one embodiment, the length $L_1$ of the individual coil member is approximately 16.5 mm. The coil member is also stored in this elongated state when packaged and retains this elongated shape after transfer into a delivery sheath and then delivered to the target vascular site as shown in FIG. 8A. As the occlusion device is deployed, these larger coiling members are allowed to recover to their large curl diameter and begin to facilitate anchoring as shown in FIG. 8B.

In one embodiment, three coiling members may have a smaller curl diameter and a lower material modulus (e.g., softer) (e.g., coiling member 12b). As indicated in FIGS. 3B-1 to 3B-2, which show exemplary dimensions of the smaller curl coiling member 12b of FIG. 2, the smaller curl size may vary in diameter $D_3$ from approximately 9 mm to approximately 6 mm. In other embodiments the curl diameter $D_3$ may vary in a range from less than approximately 6 mm to greater than approximately 9 mm. FIG. 3B-3 illustrates this smaller coiling member 12b in a pre-deployed or storage state. In one embodiment, the diameter $D_4$ of the individual coil member is approximately 0.018 mm. In other embodiments, the diameter $D_4$ of the individual coil member is between approximately 0.016 mm and 0.020 mm. In one embodiment, the length $L_2$ of the individual coil member is approximately 16.5 mm. The coil member 12b is also stored in this elongated state when packaged and retains this elongated shape after transfer into a delivery sheath and then delivered to the target vascular site as shown in FIG. 8A. As the occlusion device is deployed, these small coiling members are allowed to recover to their small curl diameter and begin to facilitate filling in and packing the coil pack as shown in FIG. 8B.

In some embodiments, the curl diameter of the coiling member 12a, 12b is determined relative to the diameter of the vessel (e.g., a peripheral artery, peripheral vessel, or biological lumen) to be occluded. In some embodiments, the curl diameter $D_1$ of the larger coiling members 12a may be approximately 20% to approximately 70% greater than the diameter of the vessel and the curl diameter $D_3$ of the smaller coiling members 12b is less than the diameter of the particular vessel. For example, anatomical vessels may range in diameter from approximately 1 mm up to approximately 18 mm. So, for a vessel having a diameter of 6 mm, the curl diameter of the larger coiling members 12a may range from approximately 7.2 mm to approximately 10.2 mm such that they can anchor the occlusion device in place and the curl diameter of the smaller coiling members 12b is less than 6 mm such that they can curl/coil unobstructed by the vessel wall and generate a tight coil pack.

A typical single embolic coil may be formed and provided in a tapered configuration (e.g., a Tornado coil). This configuration is commonly used by single coil manufacturers to make the single coil more tolerant of different vessel diameters and of physician error of vessel size measurement. Generally, tapered coils are offered as a single embolic coil delivered through a catheter that incorporates a smaller curl diameter at one end transitioning once to larger curl diameter along its total length.

The presently disclosed device is unique in that it uses a smaller to larger curl diameter transition in multiple instantiations along the length of one coiling member, with a unique period/frequency for that curl size transition that does not synchronize with the adjoining coiling member. Multiple coiling members then do not synchronize along the length of the occlusion device which specifically enhances the reliability of the coiling members interacting (intermeshing) during deployment to achieve a dense coil pack. Further the coiling member curl transition is formed such that the small curl diameter nests inside the larger curl diameters so that instead of forming a tapered coil appearance, the coiling members form a pinwheel shape (curls lie in a single plane) and then replicate multiple pinwheels along the length of the coiling member again in unique periods to avoid synchronization.

Figures 1, 4A:
Figures 2, 4A:
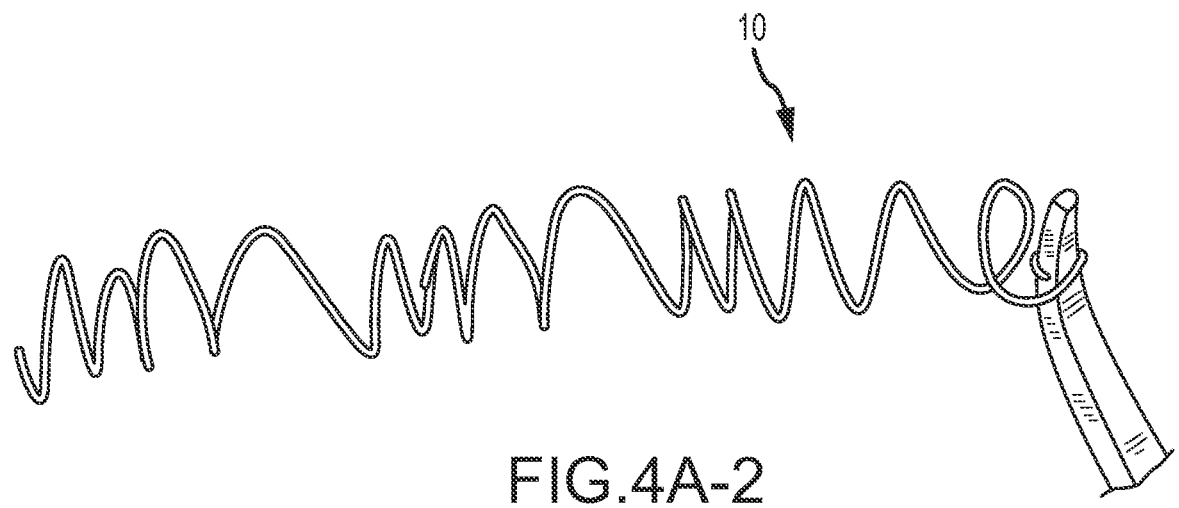

As shown in FIGS. 4A-1 and 4A-2, an exemplary coiling member 10 is shown in a slightly expanded resting state. The repeating variation in the curl diameter is shown as well as the coiling members being partially nested within the transition. In one embodiment, the coils are formed in a series of curls in repeating pinwheel shapes. FIG. 4A-2 illustrates the coil of FIG. 4A-1 in an expanded or stretched state to show the repeating period of the curl diameter change.

This multiple, non-synchronous curl diameter transition is uniquely beneficial to minimizing prolapse and bucking with the multi-coiling member device. In use, the initial loops of the large curl diameter coiling members 12a exit from the delivery sheath and they extend radially to contact the vessel wall 120 for anchoring through the first 1-2 loops. The rapid transition to smaller diameters allow the following loops to collapse and facilitate stabilizing the coil pack before additional larger curl diameter loops are deployed. This transition is advantageous because if additional large curl diameter loops were to continue to be deployed from the delivery sheath (as if the coiling members appeared like a simple helical coil, common with other embolic coils), these loops would not collapse into the coil pack but would instead be inhibited from curling by the first loops and the following coiling members would extend down the vessel as prolapse. Instead, the disclosed device's repeating pinwheel coiling members follow the first 1-2 anchoring loops with smaller curl diameters that allow curls to collapse to better fill in the internal space (see, e.g., FIGS. 8A-8F). The smaller curl diameters minimize the potential for the coiling members to extend down the vessel while reliably forming a dense coil pack.

The coiling members 10 may be fabricated initially as stands, strings, wires, fibers, threads, or other elongate members from a variety of materials. In one embodiment, the coiling members are made of a radiopaque, crosslinked, thermoset polymer which maintains the ability to recover to its curl shapes even after years of being stored in an elongated configuration in the package. These polymers may also exhibit shape memory functionality (thermal stimulus) but this functionality is not required for this application. In other embodiments, the coil members may be elongate members made from other materials capable of recovering to the desired curled shape after being packaged in the elongated, stored configuration. This includes, for example, a shape memory metal alloy or other materials, including metals such as stainless, platinum, nitinol or polymer/plastics, such as thermoplastic or thermoset resins, or a combination of any of the foregoing.

Figure 5:
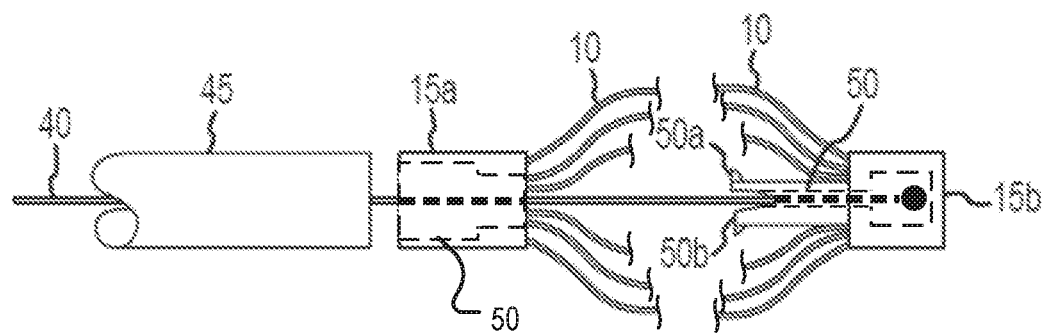
FIG. 5 illustrates a distal and proximal retaining feature of the device of FIG. 1A, the distal retaining feature including an engagement feature.
Figure 6:
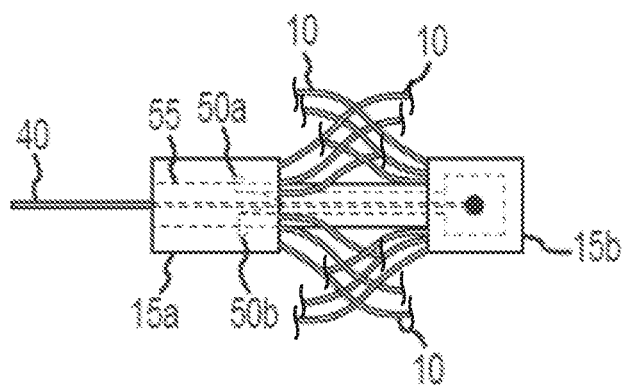
FIG. 6 depicts the proximal and distal retaining features of FIG. 5 engaged via the engagement feature.

Returning now to FIGS. 1 and 2, and with reference to FIGS. 5-6, the individual coiling members 10 having varying curl diameters are joined at their distal ends by a single distal nubbin or retaining feature 15b. All of the coiling members 10 are aligned during production of the device 5 such that a loop of the largest curl diameter 12a is joined at the distal nubbin so that the largest curls can form a basket of loops when the device is deployed (see, e.g., FIGS. 8A-8F). This basket is defined as Zone 1 in FIG. 1. However, the coiling members varying curl diameters transition on different periods so as not to be in synchronous phase along the entire length of the device. The intentional lack of synchronicity improves the randomness of the loop position within the coil pack and increases the overall density of the coil pack. Increased density improves the mechanical flow blockage thereby minimizing the time to occlusion.

Because the device uniquely employs multiple coiling members in parallel, there is increased risk that one or more of these members may not move in concert with the other(s) and may become errant in position. Errant coiling members can result in prolapse and/or bucking. The asynchronous, varying curl diameter along the length of the coiling members helps to reduce errant coiling member behavior by encouraging the coiling members to become entangled during deployment. In addition, restraining loops 17 are employed along the length of the device to minimize errant behavior of individual coiling members. As shown in FIG. 1 and others, in some embodiments, the device 5 may also include a restraining loops 17 configured to join some or all of the individual coil members 10 at one or more locations along the length of the occlusion device. The loop 17 limits the free length of every coiling member to prevent any member from extending downstream of the vessel and causing prolapse. When the coil is in its elongated state (see, e.g., FIGS. 3A-3 and 3B-3), the restraining loop 17 is placed around all of the coils members in the set at multiple locations, e.g., approximately 3 cm and approximately 5 cm from the distal end of the coil member. The loop 17 is adhered to one or more of the coiling members at that location (e.g., bonded). The loop may be made of polymer tubing or nylon fiber, or other appropriate material that is joined into a ring. In some embodiments, the restraining loop may also be a clip. The loops can be sized to be relatively small in diameter so as to tightly constrain the set of coiling members during deployment to a size not much larger than their pre-deployed diameter. In other embodiments, the loops can be sized to be somewhat larger in diameter, slightly constraining or loosely holding the coiling members during deployment to a size larger than the pre-deployed device but smaller than the diameter of the vessel. This loop may also temporarily capture a feature of the retaining/detaching mechanism, e.g. distal control wire during deployment.

As the loops are affixed to at least one coiling member at each location, they act as constraining elements, limiting the "free length" of each coil so that long free loops of coil cannot be achieved that would otherwise extend down the vessel resulting in prolapse. During deployment, when the distal end is captured on the distal control wire, the coiling members are anchored at the distal end and the loops constrain all coiling members to limit their free length, minimizing the potential for prolapse. Further, the first restraining loop place a specific distance from the distal end will constrain the coiling members around the distal control wire such that the curls formed (with the largest curl diameter on the coiling members synchronized at this end) will form a large basket or flower-like structure which extends outward to the diameter of the vessel. This basket inhibits the following curls of coiling members from prolapsing downstream as they engage with the basket. Subsequently, this first length of the device, from distal end to the first restraining loop, fills the diameter of the vessel up against the vascular wall and as such, it works as an "anchoring zone" (see, e.g., FIG. 1A).

Returning now to FIG. 1A, the device 5 can be described in terms of functional "zones" where the coil members 10, retaining features 15 and restraining loop(s) 17 act together to carry out specific functions. For example, in zone 1, the distal nubbin 15b and restraining loop 17a and the coil members therebetween provide an anchor function of the device as mentioned previously. The coil members between the distal nubbin 15b and restraining loop 17a can form a basket-like structure or other similar anchoring structure such that upon deployment into the vessel, the coil members anchor outward against the vessel wall to prevent further coiling member movement and eventually result in stable vessel occlusion. These anchoring coiling members may be made from a stiffer material and formed into the largest curl diameter within the device. In zone 2, defined as the coiling members between the restraining loop 17b and the proximal nubbin 15a, the coiling members may be made from a softer material and formed to have varying, smaller, curl diameters to minimize prolapse and encourage coil pack stability. In some embodiments, the device may include a third zone with coiling members similar to Zone 1 for symmetry of upflow and downflow applications, or may provide additional smaller but stiffer coiling members to facilitate ease of device delivery down a catheter or sheath. A stiffer proximal zone on the device reduces compaction of the device within the catheter or sheath during delivery. Reduced compaction reduces friction and thereby reduces the delivery force.

Figures 6A, 6B:
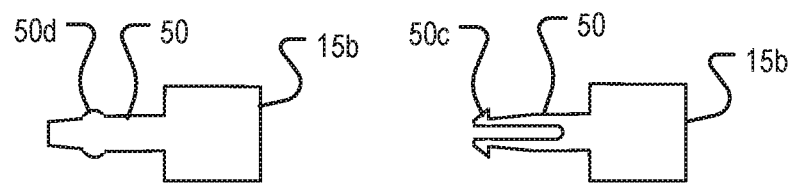
FIGS. 6A and 6B are schematic illustrations depicting alternate embodiments of an engagement feature.

In one embodiment, and as shown in FIGS. 5 and 6, the distal retaining feature/nubbin 15 b may further include an engagement feature 50. The engagement feature 50 may be a tube-like feature that extends from the distal nubbin 15b proximally. The feature 50 may have a detent 50c as shown in FIG. 6A or small tabs 50a, 50b that engage the inner circumference 55 of the proximal nubbin 15a as shown in FIGS. 5 and 6. The engagement feature 50 on the distal nubbin engages the inner circumference 55 of the proximal nubbin, thereby causing the nubbins 15 to lock together. That is, when the distal and proximal nubbins 15b, 15a are compressed together during release, the engagement feature 50 locks the two nubbins together at release. In other embodiments, both nubbins may include engagement features, such as complimentary hooks 50c as shown in FIG. 6B configured to engage each other or the proximal nubbin 15 a may include a hook 18a configured to engage a hole 18b in the distal nubbin 15b (see FIG. 1). Engagement of the two ends 15a, 15b enhances the radial expansion of the coil pack by encouraging a compressed, and stable, axial dimension. The engagement feature 50 hinders or prevents the device from relaxing axially after release which may reduce radial expansion and reduce the ability of the coil pack to anchor in the vessel.

In use, and as described in more detail below with reference to FIGS. 7-8E (and with reference to FIGS. 5-6), the distal end nubbin 15b is held on a distal control wire 40 at a fixed distance past the distal end 110 of the delivery sheath 115. In one embodiment, this distance is approximately 1.5 cm distal to the end of the sheath. As the pusher 45 advances the proximal end nubbin 15a, it slides along the distal control wire 40 as the coiling members are expelled and deployed out of the sheath. Eventually, the proximal end nubbin 15a is directly opposed (opposite) the distal end nubbin 15b commonly aligned by the distal control wire 40. When the two nubbins 15 are positioned opposed to each other, all of the coiling members have been deployed out of the delivery sheath. The pusher is stabilized, fixing the proximal nubbin just beyond the distal end of the sheath and the distal control wire is retracted. As it retracts, it is released from the distal end nubbin. As the distal control wire is further retracted, it causes the proximal nubbin to be released, separating the occlusion device from the pusher, distal control wire and sheath. At this point, the device has been completely deployed and released into the vessel.

Figure 7:
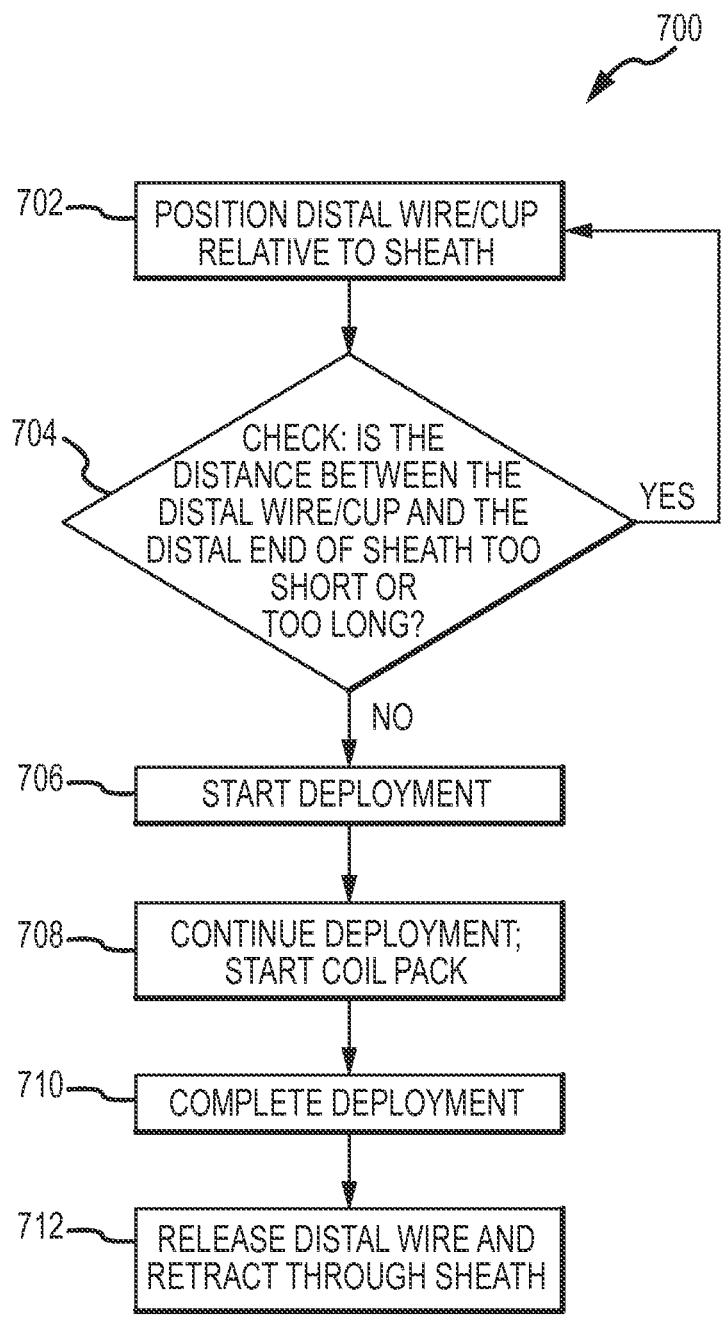
FIG. 7 is a flow chart illustrating a method of deploying the occlusion device according to aspects of the present disclosure.
Figure 8C:
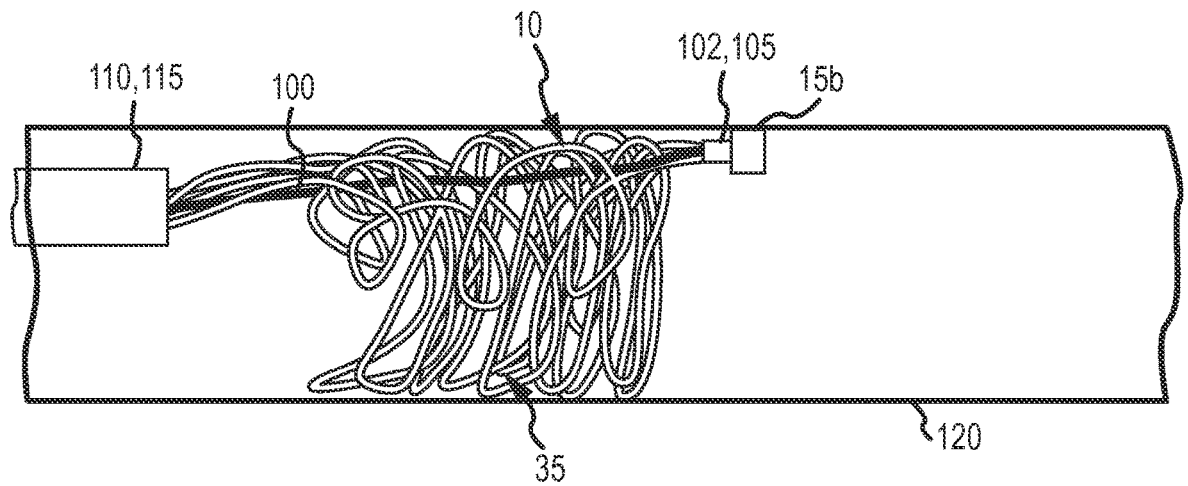
Figure 8D:
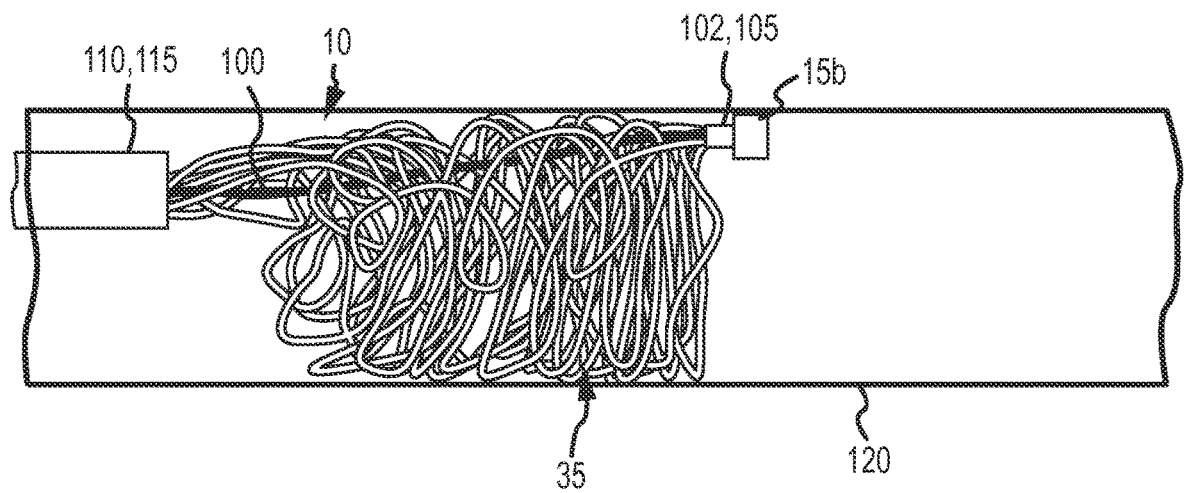
Figure 8E:
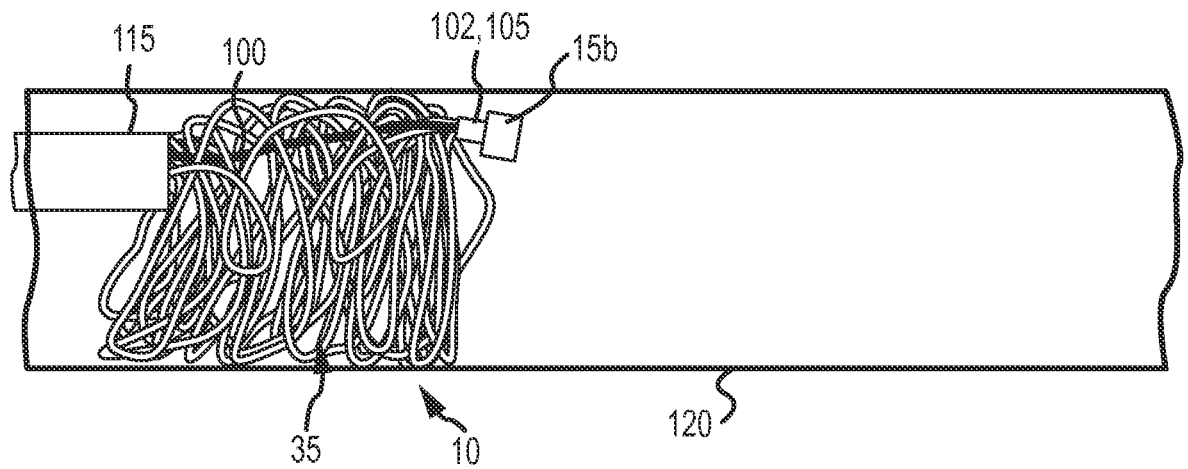
Figure 8F:
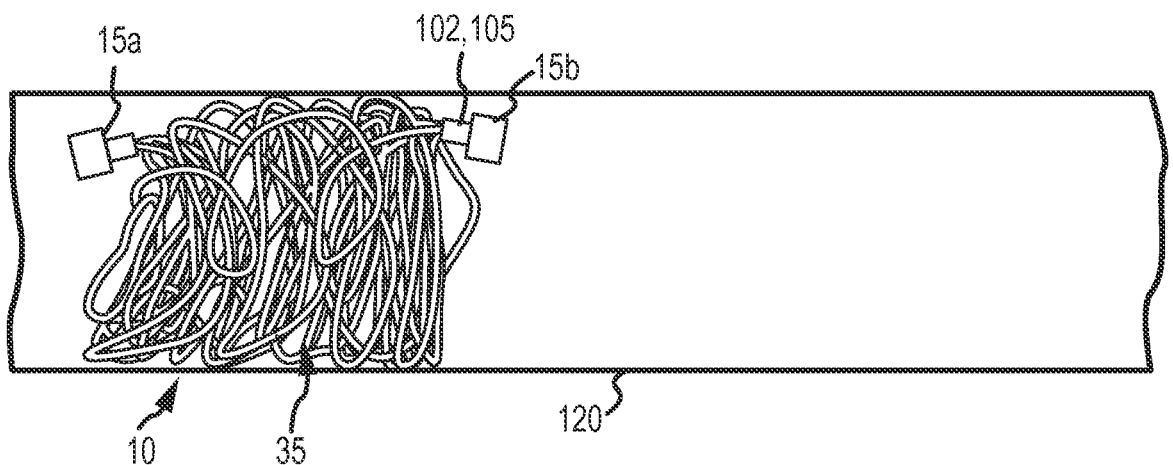

For a discussion of use of the lumen occlusion device as disclosed herein, reference is now made to FIGS. 7-8F, which include a flow chart depicting a method of using/deploying the device and an exemplary occlusion device shown in various states of deployment. As can be generally understood with reference to FIGS. 7-8F, and others, this disclosure describes a peripheral vascular occlusion device 5 wherein multiple, very small coiling members 10 (fibers, tendrils, or similar structures) are delivered simultaneously to form a coil pack (for example, a coil pack 35 as described with reference to FIGS. 8D and 8E) that would otherwise be formed by the accumulation of individual coils delivered sequentially. This simultaneous delivery and rapid formation of a coil pack provides key benefits to a vascular or biological lumen occlusion device. This configuration also provides a flexible and adaptive structure for filling aneurysm sacks or other vascular structures or other biological lumens.

As indicated in FIGS. 7-8F, while the discussion herein relates to occluding a vessel, it is understood that the device 5 may be utilized for other vascular malformations, such as embolization of uterine fibroids or varicoceles, among other uses. The target sites may present a variety of vessel sizes as determined by the physician using clinical imaging techniques. The disclosed vascular or lumen occlusion device may be sized to be used with different vessel sizes and may require the use of different size delivery catheters and sheaths. The disclosed occlusion device may be provided in various sizes to occlude vessels between approximately 1 mm and approximately 16 mm in diameter.

In use, and in accordance with the exemplary method 700, the device 5 is loaded into a catheter or other delivery device in a non-expanded (or pre-deployed or storage) state. Once the surgeon has placed the delivery device into the proper location, the device 5 may be pushed by a "pusher" 45 out of the delivery device (e.g., a sheath 115 or catheter). The straightened coiling members 10 (in non-expanded shape) are deployed by advancing the occlusion device down the delivery device, using a pusher, and pushing it out the distal end of the delivery device at the target occlusion site. It should be appreciated that the operations of the method 700 may be performed in the order illustrated, in another suitable order and/or one or more operations may be performed simultaneously. Moreover, in some embodiments, the method 700 may include more or fewer operations than those illustrated.

In accordance with the exemplary method 700, in operation 702, and as illustrated in FIG. 8A, the device 5 includes a detachment feature, such as a distal ball 102 and distal wire 100 with a distal cup 105 (with a precision opening) attached to the distal nubbin 15b. The distal ball 102 and wire 100 is advanced to position the cup 105 at a specified distance beyond the distal end of the sheath. In one embodiment, that distance may be approximately 1.5 cm beyond the end of the distal sheath. In operation 704, the distance between the cup and the distal end 110 of the sheath 115 is determined. In one embodiment, this determination is made by monitoring the position of the device on a fluoroscope monitor or other clinical medical imaging system in which the device may be seen. This position is important to help maintain a tight coil pack—if this dimension is too short, it's too hard to push out the coils. If this dimension is too long, it results in a loose coil pack.

Recall that the coil ends are bonded together into the distal nubbin. The distal cup 105 is then bonded (added component) on the nubbin to facilitate the delivery and release of the device. In one embodiment, the distal nubbin 15b and cup 105 may be the same element. The nubbin 15b has a through-hole to allow the distal wire 100 to pass through the nubbin into the distal cup. In FIG. 8A, the distal wire 100 is seen lying alongside the coiling members in their straightened, pre-deployed condition—this is the configuration of how they move down the catheter during "delivery." At the end of the distal wire 100 is a small metal ball 102. It is captured within the plastic cup 105. In one embodiment, the wire passes through a precision opening that is intentionally smaller than the ball causing the distal cup to be retained on the distal wire until a certain force is exceeded in which the ball pulls through the precision hole (stretching the plastic cup) to release.

In operation 706, and as illustrated in FIG. 8B, deployment of the device begins. In one embodiment, there are seven coiling members 10 in the device 5 that attach to the distal nubbin. In some embodiments, the multiple coiling members 10, in a deployed state, may have complex curl shapes, multiple size curls and/or multiple sizes with respect to either diameter, length, or both. In various embodiments, some coiling members may be produced larger in diameter than others to be stiffer and thereby assist in anchoring the coil pack. Other coiling members for use in the same device may be produced softer, i.e., of a smaller diameter, to assist in quickly filling the pack and minimizing the coil pack length. The curl diameters of these coils are aligned such that all of the large diameters are bonded together into the distal nubbin 15b. As such, when the device is initially deployed these large curls extend out to the sidewalls of the vessel 120. These large curl shapes may be distributed around the distal control wire, or in a large group of loops to one side, as shown in FIG. 8B. While there is some randomness to this behavior, however in all conditions, the result is a "basket" or "backstop" for the remaining coils to pack against. Getting the initial coils to form this basket at the distal cup aids in reducing any propensity for distal prolapse (where coils travel significantly past the cup and downstream in the vessel). The basket is a result of: 1) distal ends bonded into the distal nubbin; 2) large curl sizes together into the distal nubbin; and 3) an intermediate restraining loop 17 that keeps the proximal end of this curl segment constrained around the distal retaining wire before release.

Operation 708, as illustrated in FIG. 8C, shows the device in mid-deployment. In mid-deployment, the variation in curl size can be seen to enable a non-uniform curling of the coils 10 but encourage a random, chaotic coil pack to enhance density and improve the amount of mechanical flow obstruction from this material.

In accordance with operation 710, as illustrated in FIG. 8D, deployment is completed. When all of the coils are deployed (advanced and expelled from the sheath 115 as the pusher 45 has been advanced), the coil pack 35 is complete and provides significant mechanical flow reduction. In one embodiment, nylon (fuzzy) fibers, attached to some of the coiling members, encourage thrombus formation and provide a lattice for thrombus adherence, to avoid releasing the thrombus where it may float downstream (see, e.g., FIG. 1B). Thus, the intended result is achieved when the coil pack is placed in the intended position within the vessel, the coil pack is anchored against the vessel wall to avoid migration due to the blood flow, the coil pack is dense to provide a high degree of mechanical flow blockage, and thrombus has formed on the coil pack, adhering to the nylon fibers resulting in complete vessel occlusion.

Once deployment is complete, and in accordance with operation 712, as illustrated in FIG. 8E, release occurs when the distal wire 100 is pulled back (retracted). In one embodiment, this retraction applies sufficient force to overcome the interference of the ball and precision opening in the distal cup 105. The distal cup 105 "pops" free and the wire is retracted back into the delivery sheath. FIG. 8F illustrates that the resulting pack 35 is complete and compact and the distal wire 100 has been retracted back into the delivery sheath (not shown).

The vascular or biological lumen occlusion device disclosed herein provides benefits including the following: reduced procedure time, reduced procedure cost, improved ease of use and improved occlusive outcome relative to other comparable devices. The unique features of the device include proximal and distal ends permanently joined into nubbins; engagement features on each nubbin to achieve a connection or lock during deployment; specific coils designed for specific functions and features that minimize prolapse and help to assure predictable coil pack formation during deployment.

Thus, as can be understood from the discussion found herein, the device and its various configurations as disclosed herein address current key clinical deficiencies that are unmet with existing single metal or single polymer coils and with other vascular occlusion devices, such as metal mesh plugs, and their associated challenges discussed herein.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter are used interchangeably for purposes of this description. The exemplary drawings are for purposes of illustration only and the dimensions, positions, order and relative sizes reflected in the drawings attached hereto may vary.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A vascular or biological lumen occlusion device for occluding at a target location comprising:
   a plurality of individual coiling members made of a material having a shape recovery capability and formed with respective, preset non-uniform variations of curl diameters, each member having a proximal end and a distal end;
   a proximal retaining feature coupled to the proximal ends of the plurality of coiling members to join the proximal ends together; and
   a distal retaining feature coupled to the distal ends of the plurality of coiling members to join the distal ends together, wherein
   one of the proximal retaining feature or the distal retaining feature defines a first engagement feature having a hook-like feature and the other of the proximal retaining feature or the distal retaining feature defines a second engagement feature having an opening configured to receive at least a portion of the hook-like feature;
   in a predeployed state, the hook-like feature and the opening are spaced apart from one another such that the hook-like feature is either entirely distal to or entirely proximal to the opening, and the individual coiling members are constrained in an elongate form and arranged in parallel; and
   in a deployed state, the hook-like feature and the opening are connected to one another and the individual coiling members are in a released form to recover the preset non-uniform variations of curl diameters to form a random, chaotic dense coil pack.

2. The device of claim 1 further comprising at least one restraining loop coupled to some or all of the plurality of individual coiling members along a length of the coiling members.

3. The device of claim 1 further comprising nylon fibers coupled to one or more of the plurality of individual coiling members to promote thrombus formation.

4. The device of claim 1, wherein the coiling members are made from radiopaque polymers, radiopaque crosslinked, thermoset polymers, or radiopaque shape memory polymers.

5. The device of claim 1, wherein each of the coiling members has a coil diameter of approximately 0.018 mm.

6. The device of claim 1, wherein the hook-like feature and the opening remain connected to one another upon formation of the random, chaotic dense coil pack and recovering of the preset non-uniform variations of curl diameters.

7. The device of claim 1, wherein
   a first coiling member of the plurality of individual coiling members defines a first portion having a first curl diameter and a second portion having a second curl diameter that is smaller than the first curl diameter;
   the first portion of the first coiling member is configured to anchor the lumen occlusion device in the target location; and
   the plurality of individual coiling members are configured to fill the target location and create the dense coil pack.

8. The device of claim 7, wherein the first portion has a first material modulus and the second portion has a second material modulus.

9. The device of claim 7, wherein
   the first curl diameter is between approximately 12 mm and approximately 8 mm; and
   the second curl diameter is between approximately 9 mm and approximately 6 mm.

10. The device of claim 7, wherein a vascular or biological lumen defines a lumen diameter;
    the first curl diameter is between approximately 20% and approximately 70% greater than the lumen diameter; and
    the second curl diameter is less than the lumen diameter.

11. The device of claim 1, wherein
    a first coiling member of the plurality of individual coiling members defines a first curl diameter;
    a second coiling member of the plurality of individual coiling members defines a second curl diameter that is smaller than the first curl diameter, and
    the first coiling member is configured to anchor the lumen occlusion device in the target location and the second coiling member is configured to fill the target location and create the dense coil pack.

12. The device of claim 11, wherein the first member of the plurality of individual coiling members further includes a third curl diameter that is smaller than the first curl diameter.

13. The device of claim 12, wherein the second member of the plurality of individual coiling members further includes a fourth curl diameter that is smaller than the second curl diameter.

14. The device of claim 1, wherein
    a first one of the individual coiling members has a first material modulus and a second one of the individual coiling members has a second material modulus.

15. The device of claim 14, wherein the second material modulus is less than the first material modulus.

16. The device of claim 1, further comprising a control wire associable with the distal retaining feature and configured to manipulate the distal retaining feature for connection with the proximal retaining feature.

17. The device of claim 16, wherein the control wire has a rigidity greater than individual ones of the plurality of coiling members.

18. A method of manufacturing a lumen occlusion device comprising
- providing a plurality of flexible elongate members made of a material capable of recovering a preset curl shape formed therein;
- forming a plurality of coiled members from the plurality of flexible elongate members, wherein each of the coiled members is curled with respective preset non-uniform variations of curl diameters;
- constraining the plurality of the coiled members in a pre-deployed state as a plurality of elongate members in parallel with each other, but which remain capable of coiling to recover the preset non-uniform variations of curl diameters in the form of the plurality of coiled members, wherein each of the plurality of elongate members has a proximal end and a distal end;
- coupling the distal ends of the plurality of elongate members together with a distal retaining feature; and
- coupling the proximal ends of the plurality of elongate members together with a proximal retaining feature, wherein
- one of the distal retaining feature or proximal retaining feature defines a first engagement feature having a hook-like feature and the other of the distal retaining feature or the proximal retaining feature defines a second engagement feature having an opening configured to receive at least a portion of the hook-like feature;
- in the pre-deployed stated, the hook-like feature and the opening the distal retaining feature and the proximal retaining feature are spaced apart detached from one another such that the hook-like feature is either entirely distal to or entirely proximal to the opening; and
- the hook-like feature and the opening the distal retaining feature and the proximal retaining feature are moveable relative to one another to define a deployed state in which the hook-like feature and the opening the distal and proximal retaining features are connected to one another.

19. The method of claim 18, further comprising one of
- forming a first coiled member of the plurality of coiled members to have a first curl diameter between 20% and 70% greater than a target lumen diameter and a first material modulus; or
- forming a second coiled member of the plurality of coiled members with a second curl diameter smaller than the target lumen diameter and a second material modulus.

20. The method of claim 18, further comprising
- providing a delivery device having a pusher mechanism and a detachment feature; and
- operably attaching the distal retaining feature to the detachment feature.

21. The method of claim 18, further comprising one of coupling some or all of the plurality of elongate members together with a retaining loop, or coupling nylon fibers to a portion of one or more of the plurality of elongate members to promote thrombus formation.

22. A method of occluding a vascular or biological lumen comprising
- introducing a lumen occlusion device pre-loaded in a delivery device to a target location, the lumen occlusion device comprising
  - a plurality of individual coiling members made of a material having a shape recovery capability and formed with respective, preset, non-uniform variations of curl diameters, each member having a proximal end and a distal end;
  - a proximal retaining feature coupled to the proximal ends of the plurality of coiling members to join the proximal ends together;
  - a distal retaining feature coupled to the distal ends of the plurality of coiling members to join the distal ends together, wherein
- one of the proximal retaining feature or the distal retaining feature defines a first engagement feature having a hook-like feature and the other of the proximal retaining feature or the distal retaining feature defines a second engagement feature having an opening configured to receive at least a portion of the hook-like feature;
- in a predeployed state, the hook-like feature and the opening are spaced apart from one another such that the hook-like feature is either entirely distal to or entirely proximal to the opening, and the individual coiling members are constrained in an elongate form and arranged in parallel; and
- in a deployed state, the hook-like feature and the opening are connected to one another and the individual coiling members are in a released form to recover the preset non-uniform variations of curl diameters to form a random, chaotic dense coil pack; and
- deploying the occlusion device at the target location.

23. The method of claim 22, wherein
- a first coiling member of the plurality of individual coiling members has a first curl diameter and a first material modulus and a second coiling member of the plurality of individual coiling members has a second curl diameter and a second material modulus; and
- the deploying operation further comprises deploying the first coiling member to anchor the device in the target location and deploying the second coiling member to fill the target location and create the dense coil pack.

24. The method of claim 22, further comprising placing the lumen occlusion device in one of a peripheral vessel thereby occluding the peripheral vessel for treatment of uterine fibroids, varicoceles or internal hemorrhage, or a peripheral artery thereby occluding the peripheral artery before undertaking other procedures including one or more of placing a port or injecting a chemotherapy agent, or in a biological lumen selected from the group consisting of a fallopian tube, a lung lobe, or a bile duct.

25. The method of claim 22, wherein
- the device further includes a detachment feature coupled to the distal retaining feature; and
- the deploying operation further comprises releasing the detachment feature from the delivery device.

26. The method of claim 25, further comprising positioning the occlusion device by advancing the detachment feature past a distal end of the delivery device to a position in the target location that will result in the occlusion device forming a dense coil pack.

27. The method of claim 26, further comprising
- disengaging at least a portion of the detachment feature from the distal retaining feature; and retracting the portion of the detachment feature back into the delivery device without removing the dense coil pack.

* * * * *